US009383363B2

(12) United States Patent
Butt

(10) Patent No.: US 9,383,363 B2
(45) Date of Patent: Jul. 5, 2016

(54) LASP-1, A NOVEL URINARY MARKER FOR TRANSITIONAL CELL CARCINOMA DETECTION

(71) Applicant: Elke Butt, Würzburg (DE)

(72) Inventor: Elke Butt, Würzburg (DE)

(73) Assignee: Julius-Maximilians-Universität-Würzburg, Würzburg (DE)

( * ) Notice: Subject to any disclaimer, the term of this patent is extended or adjusted under 35 U.S.C. 154(b) by 0 days.

(21) Appl. No.: 14/363,064

(22) PCT Filed: Dec. 6, 2012

(86) PCT No.: PCT/EP2012/074634
§ 371 (c)(1),
(2) Date: Jun. 5, 2014

(87) PCT Pub. No.: WO2013/083690
PCT Pub. Date: Jun. 13, 2013

(65) Prior Publication Data
US 2014/0370530 A1    Dec. 18, 2014

(30) Foreign Application Priority Data
Dec. 8, 2011   (EP) .................................... 11009694

(51) Int. Cl.
| G01N 33/53 | (2006.01) |
| G01N 33/574 | (2006.01) |
| G01N 33/493 | (2006.01) |
| A61B 1/307 | (2006.01) |
| H01J 49/26 | (2006.01) |

(52) U.S. Cl.
CPC .......... *G01N 33/57438* (2013.01); *A61B 1/307* (2013.01); *G01N 33/493* (2013.01); *G01N 33/57407* (2013.01); *G01N 33/57488* (2013.01); *H01J 49/26* (2013.01)

(58) Field of Classification Search
CPC ........... C12Q 1/6886; C12Q 2600/158; C12Q 2600/136; C12Q 2600/118; C12Q 1/6883; C12Q 2600/112; G01N 33/57407; G01N 33/57488; G01N 33/493; G01N 33/57434; G01N 21/6428; G01N 21/6458; G01N 2570/00
See application file for complete search history.

(56) References Cited

U.S. PATENT DOCUMENTS

| 2004/0009479 | A1* | 1/2004 | Wohlgemuth et al. ............ | 435/6 |
| 2004/0043436 | A1 | 3/2004 | Vlahou et al. | |
| 2010/0152055 | A1* | 6/2010 | Kozono et al. ..................... | 506/9 |
| 2011/0262921 | A1* | 10/2011 | Sabichi et al. ............... | 435/6.12 |

FOREIGN PATENT DOCUMENTS

| EP | 1930426 | 6/2008 |
| WO | 2006020302 | 2/2006 |

OTHER PUBLICATIONS

Mayeux et al. ("Biomarkers: Potential uses and Limitations"; NeuroRx (2004); vol. 1, pp. 182-188).*
Butt et al., (Journal of Biochemical Chemistry, vol. 278, No. 18, Issue of May 2, pp. 15601-15607, 2003.*
International Search Report from corresponding International Application No. PCT/EP2012/074634 dated May 14, 2013.
Takeshi Chiyomaru et al: "Functional role in LASP1 in cell viability and its regulation by microRNAs in bladder cancer", Urologic Oncology: Seminars and Original Investigations, vol. 30, No. 4, Sep. 16, 2010, pp. 434-443.
Chiyomaru T. et al: "Oncogenic LASP1 is Directly Regulated by the Tumor Suppressive MicroRNAs (MIR-1, MIR-218, and MIR-133A) in Bladder Cancer", European Urology Supplements, vol. 10, No. 2, Mar. 2011, p. 79.
Vlahou A. et al: "Development of a novel proteomic approach for the detection of transitional cell carcinoma of the bladder in urine.", The American Journal of Pathology Apr. 2001, vol. 158, No. 4, Apr. 2001, pp. 1491-1502.
Chao D. et al: "Bladder cancer 2000: molecular markers for the diagnosis of transitional cell carcinoma.", Reviews in Urology Spring 2001, vol. 3, No. 2, Apr. 2001, pp. 85-93.
Chew, C S et al: "LASP-1 Is a Regulated Phosphoprotein Within the Camp Signaling Pathway in The Gastric Parietal Cell", American Journal of Physiology, American Physiological Society, United States, vol. 275, No. 1, Jul. 1, 1998, pp. C56-C67.
Grunewald Thomas GP et al: "The LIM and SH3 domain protein family: structural proteins or signal transducers or both?", Molecular Cancer, Biomed Central, London, GB, vol. 7, No. 1, Apr. 17, 2008, p. 31.
T G P Grunewald et al: "Overexpression of LASP-1 mediates migration and proliferation of human ovarian cancer cells and influences zyxin localization", British Journal of Cancer, vol. 96, No. 2 Jan. 9, 2007, pp. 296-305.
James W F Catto et al: "MicroRNA in Prostate, Bladder, and Kidney Cancer: A Systematic Review", European Urology, Elsevier BV, NL, vol. 59, No. 5, Jan. 24, 2011, pp. 671-681.
Derya Tilki et al: "Urine Markers for Detection and Surveillance of Non-Muscle-Invasive Bladder Cancer", European Urology, vol. 60, No. 3, Sep. 1, 2011, pp. 484-492.

(Continued)

*Primary Examiner* — Shafiqul Haq
*Assistant Examiner* — Carmencita M Belei
(74) *Attorney, Agent, or Firm* — DT Ward, PC; Donna T. Ward; Lingyun Jia

(57) ABSTRACT

The invention relates to the use of LASP-1 in a urine sample obtained from a subject for diagnosing and/or grading transitional cell carcinoma. The invention furthermore relates to a method for diagnosing transitional cell carcinoma comprising detecting the presence or absence of LASP-1 in a urine sample obtained from a subject, wherein the presence of LASP-1 above 1 ng/500 μl urine is indicative for transitional cell carcinoma and a method for grading transitional cell carcinoma comprising determining the level of LASP-1 in a urine sample obtained from a subject, wherein the level of LASP-1 correlates with the grade of the transitional cell carcinoma.

3 Claims, 3 Drawing Sheets

(56) References Cited

OTHER PUBLICATIONS

Figure 1:
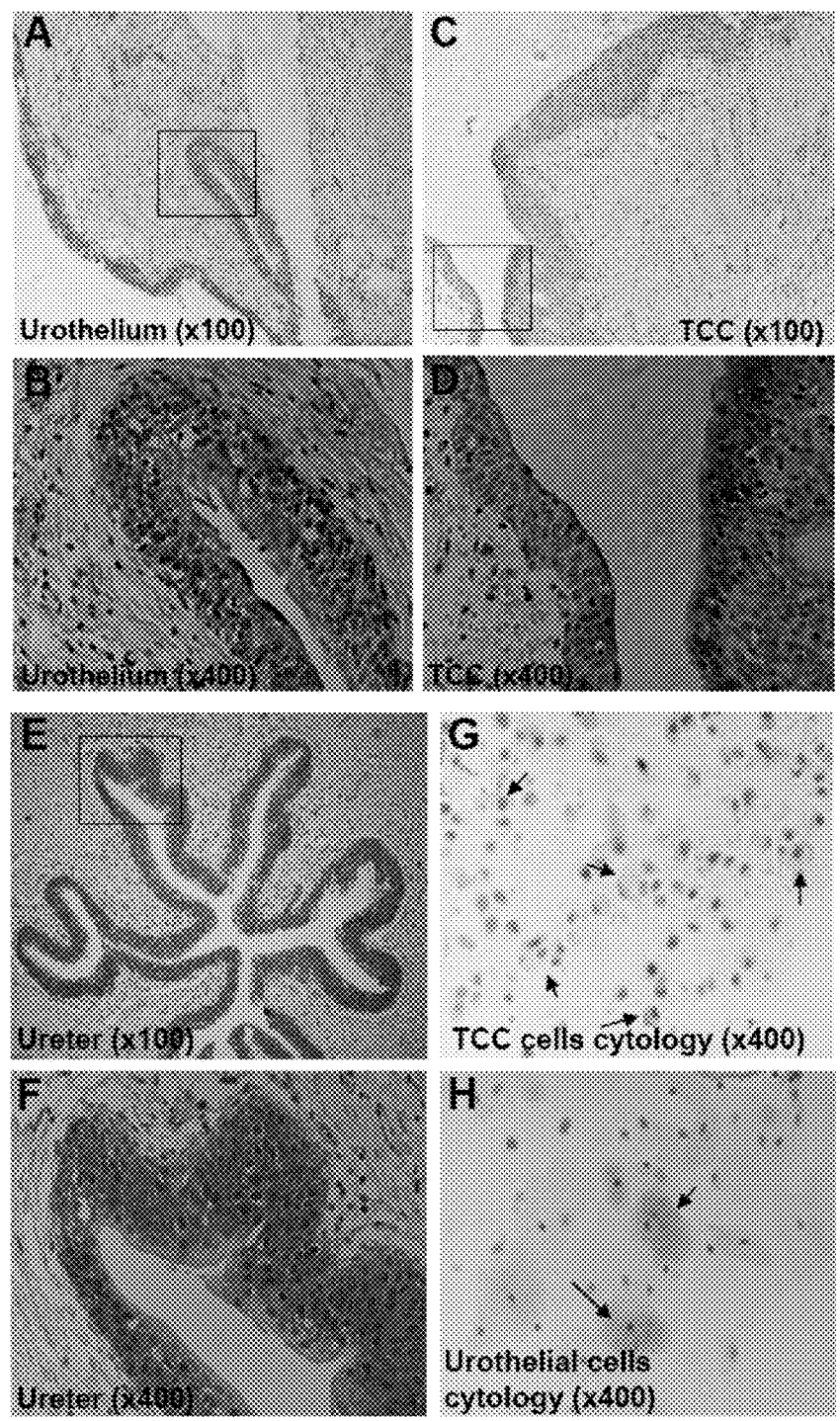

Peter Ardelt et al: "LASP-1, a Novel Urinary Marker for Detection of Bladder Cancer", Urologic Oncology: Seminars and Original Investigations, Apr. 1, 2012, XP055060488, ISSN: 1078-1439, DOI: 10.1016/j.urolonc.2012.02.002.

Babjuk M et al, EAU guidelines on non-muscle-invasive urothelial carcinoma of the bladder, the 2011 update. European urology, Jun. 2011; 59:997-1008.

Cooksley CD, et al, Clinical model of cost of bladder cancer in the elderly. Urology, 2008, 71:519-525.

Pisipati S, et al., Patients' acceptance of repeated invasive urological investigations. BJU international, 2009, 103:1453-1454.

Tilki D, et al., Urine Markers for Detection and Surveillance of Non-Muscle-Invasive Bladder Cancer. European urology, 2011, 60: 484-492.

Grunewald TG and Butt E, The LIM and SH3 domain protein family: structural proteins or signal transducers or both? Molecular cancer, 2008, 7:31.

Chiyomaru T, et al, Functional role of LASP1 in cell viability and its regulation by microRNAs in bladder cancer. Urologic oncology 2012, 30: 434-443.

Pappas CT, et al., The Nebulin family: an actin support group. Trends in cell biology 21:29-37, 2011.

Frietsch JJ, et al., Nuclear localisation of LASP-1 correlates with poor long-term survival in female breast cancer. British journal of cancer,2010, 102:1645-1653.

Grunewald TG, et al., Nuclear localization and cytosolic overexpression of LASP-1 correlates with tumor size and nodal-positivity of human breast carcinoma. BMC cancer, Oct. 23, 2007; 7:198.

Zhao L, et al., Promotion of colorectal cancer growth and metastasis by the LIM and SH3 domain protein 1. Gut, Sep. 2010; 59:1226-1235.

Chew CS, et al., Lasp-1 is a regulated phosphoprotein within the cAMP signaling pathway in the gastric parietal cell. The American journal of physiology, 1998, 275:C56-67.

Butt E et al., Actin binding of human LIM and SH3 protein is regulated by cGMP- and cAMP-dependent protein kinase phosphorylation on serine 146. The Journal of biological chemistry, 2003, 278:15601-15607.

Traenka C, et al., Role of LIM and SH3 protein 1 (LASP1) in the metastatic dissemination of medulloblastoma. Cancer research, Oct. 15, 2010; 70:8003-8014; Epub Oct. 5, 2010.

Patriarca C, et al., Cell discohesion and multifocality of carcinoma in situ of the bladder: new insight from the adhesion molecule profile (e-cadherin, Ep-CAM, and MUC1). International journal of surgical pathology, Apr. 2009; 17:99-106; Epub Nov. 19, 2008.

Yao R, et al, Altered gene expression profile in mouse bladder cancers induced by hydroxybutyl(butyl)nitrosamine. Neoplasia (New York, N.Y.), Sep.-Oct. 2004; 6:569-577.

Grunewald TG, et al., Overexpression of LASP-1 mediates migration and proliferation of human ovarian cancer cells and influences zyxin localisation. British journal of cancer, Jan. 29, 2007; 96:296-305; Epub Jan. 9, 2007.

Mihlan S, et al., Nuclear import of LASP-1 is regulated by phosphorylation and dynamic protein-protein interactions. Oncogene, Apr. 18, 2013; 32(16): 2107-2113; Epub Jun. 4, 2012.

Huber, Severine, et al., Nuclear matrix protein-22: a prospective evaluation in a population at risk for bladder cancer. Results from the UroScreen study, BJU International, Sep. 2012, vol. 110, pp. 699-708.

* cited by examiner

SEQUENCE LISTING

```
<160> NUMBER OF SEQ ID NOS: 3

<210> SEQ ID NO 1
<211> LENGTH: 261
<212> TYPE: PRT
<213> ORGANISM: Homo sapiens

<400> SEQUENCE: 1

Met Asn Pro Asn Cys Ala Arg Cys Gly Lys Ile Val Tyr Pro Thr Glu
1               5                   10                  15

Lys Val Asn Cys Leu Asp Lys Phe Trp His Lys Ala Cys Phe His Cys
            20                  25                  30

Glu Thr Cys Lys Met Thr Leu Asn Met Lys Asn Tyr Lys Gly Tyr Glu
        35                  40                  45

Lys Lys Pro Tyr Cys Asn Ala His Tyr Pro Lys Gln Ser Phe Thr Met
    50                  55                  60

Val Ala Asp Thr Pro Glu Asn Leu Arg Leu Lys Gln Gln Ser Glu Leu
65                  70                  75                  80

Gln Ser Gln Val Arg Tyr Lys Glu Glu Phe Glu Lys Asn Lys Gly Lys
                85                  90                  95

Gly Phe Ser Val Val Ala Asp Thr Pro Glu Leu Gln Arg Ile Lys Lys
            100                 105                 110

Thr Gln Asp Gln Ile Ser Asn Ile Lys Tyr His Glu Glu Phe Glu Lys
        115                 120                 125

Ser Arg Met Gly Pro Ser Gly Glu Gly Met Glu Pro Glu Arg Arg
    130                 135                 140

Asp Ser Gln Asp Gly Ser Ser Tyr Arg Arg Pro Leu Glu Gln Gln Gln
145                 150                 155                 160

Pro His His Ile Pro Thr Ser Ala Pro Val Tyr Gln Gln Pro Gln Gln
                165                 170                 175

Gln Pro Val Ala Gln Ser Tyr Gly Gly Tyr Lys Glu Pro Ala Ala Pro
            180                 185                 190
```

```
Val Ser Ile Gln Arg Ser Ala Pro Gly Gly Gly Lys Arg Tyr Arg
        195                 200                 205

Ala Val Tyr Asp Tyr Ser Ala Ala Asp Glu Asp Glu Val Ser Phe Gln
        210                 215                 220

Asp Gly Asp Thr Ile Val Asn Val Gln Gln Ile Asp Asp Gly Trp Met
225                 230                 235                 240

Tyr Gly Thr Val Glu Arg Thr Gly Asp Thr Gly Met Leu Pro Ala Asn
                245                 250                 255

Tyr Val Glu Ala Ile
            260

<210> SEQ ID NO 2
<211> LENGTH: 21
<212> TYPE: DNA
<213> ORGANISM: Artificial sequence
<220> FEATURE:
<223> OTHER INFORMATION: /note="Description of artificial sequence:
      siRNA construct targeting the LASP1 sequence"

<400> SEQUENCE: 2
aaggtgaact gtctggataa g                                           21

<210> SEQ ID NO 3
<211> LENGTH: 21
<212> TYPE: DNA
<213> ORGANISM: Artificial sequence
<220> FEATURE:
<223> OTHER INFORMATION: /note="Description of artificial sequence:
      siRNA construct targeting the LASP1 sequence"

<400> SEQUENCE: 3
aagcatgctt ccattgcgag a                                           21
```

LASP-1, A NOVEL URINARY MARKER FOR TRANSITIONAL CELL CARCINOMA DETECTION

CROSS REFERENCE TO RELATED APPLICATIONS

This application is a 35 U.S.C. §371 U.S. National Stage Entry of International Application No. PCT/EP2012/074634 filed Dec. 6, 2012, which claims the benefit of priority of European Application No.: 11009694.8, dated Dec. 8, 2011, the contents of which are each incorporated herein by reference in their entirety.

REFERENCE TO SEQUENCE LISTING

The present application is being filed along with a Sequence Listing in electronic format. The sequence Listing filed, entitled 20711000US371SEQLST, was created on Jun. 5, 2014 and is 3,205 bytes in size. The information in electronic format of the Sequence Listing is incorporated herein by reference in its entirety.

The invention relates to the use of LASP-1 in a urine sample obtained from a subject for diagnosing and/or grading transitional cell carcinoma. The invention furthermore relates to a method for diagnosing transitional cell carcinoma comprising detecting the presence or absence of LASP-1 in a urine sample obtained from a subject, wherein the presence of LASP-1 above 1 ng/500 µl urine is indicative for transitional cell carcinoma and a method for grading transitional cell carcinoma comprising determining the level of LASP-1 in a urine sample obtained from a subject, wherein the level of LASP-1 correlates with the grade of the transitional cell carcinoma.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The transitional cell carcinoma (TCC) of the urinary bladder is the most common genitourinary cancer. Men are 3-times more likely to suffer from TCC than women and the dominant age peak is the seventh decade. In 70% gross hematuria is the symptom leading patients to a urological consultation. At the time of diagnosis the majority of TCC are superficial and well treatable by transurethral resection in combination with adjuvant chemo- or immunotherapy [1]. Due to a high recurrence tendency patients need regular follow up cystoscopies, thus making TCC the socio-economic most expensive tumor entity [2].

Diagnosis of TCC currently relies on cystoscopy and urine cytology. Both examinations have limitations: A urethrocystoscopy is invasive, expensive and has a low patients acceptance [3]. Furthermore, cystoscopy has a tendency to miss flat lesions, such as carcinoma in situ while urine cytology is prone to miss well differentiated low grade lesions [1, 4]. Both methods are dependent on observer expertise. Therefore, much effort has been undertaken to improve the diagnostics of TCC, especially in the follow up care.

So far several diagnostic bladder cancer markers, mostly urine-based, have therefore been developed, e.g. nmp22 or BTA stat [4]. However, in spite of a high sensitivity their specificity is low resulting in unnecessary cystoscopies and biopsies [4]. Therefore, there is a need to identify further biological markers for identifying and grading TCC, in particular novel markers having a high sensitivity and specificity. This need is addressed by the present invention. Accordingly the present invention relates in a first embodiment to the use of LASP-1 in a urine sample obtained from a subject for diagnosing and/or grading transitional cell carcinoma.

The LIM and SH3 protein 1 (LASP-1) is a member of the LIM protein subfamily which is characterized by a LIM motif and a domain of Src homology region 3. LASP-1 is a focal adhesion protein involved in numerous biological and pathological processes [5-7] and has been linked to an oncogenic function in bladder cancer [6, 7]. Overexpression of the protein is observed in several tumor entities including breast, ovarian and colon cancer [8-10]. In breast cancer a shift of expression towards nuclear presence correlates with lymphogenic metastasis and worse overall survival of the patients. Although the function of LASP-1 is not entirely clear, it is known that the protein is involved in cytoskeletal architecture. LASP-1 seems to be constitutively expressed in fast dividing cells like lymphocytes, dendritic cells and monocytes [11] but may also promote migration and proliferation in certain cancer entities [5]. Only recently zona occludens protein 2 (ZO-2) was identified as novel LASP-1-binding partner [18]. It has been found that ZO-2 plays a role in the signal transduction pathway of LASP-1 nucleo-cytoplasmatic shuttling.

Transitional cell carcinoma (TCC) is also known as urothelial cell carcinoma (UCC) in the art. TCC is a type of cancer that typically occurs in the urinary system: the kidney, urinary bladder, and accessory organs thereof. It is the most common type of bladder cancer and cancer of the ureter, urethra, and urachus. Moreover, it is the second most common type of kidney cancer. In more detail, TCC may form in transitional cells in the lining of the renal pelvis (the part of the kidney that collects, holds, and drains urine) and in this case may be classified as kidney cancer. However, TCC has to be held distinct from renal cell carcinoma (RCC) (or hypernephroma). RCC is a kidney cancer that originates in the lining of the proximal convoluted tubule, the very small tubes in the kidney that filter the blood and remove waste products. RCC is the most common type of kidney cancer. RCC thus is often referred to in the art as kidney cancer. In accordance with the invention, TCC is preferably a tumor of the urinary bladder.

The term "urine" as used herein designates a typically sterile liquid by-product of the body that is secreted by the kidneys through a process called urination and is excreted through the urethra. Typically, about 10 mL urine are required for the uses and methods of the invention, although some lower as well as higher values are feasible. In any case, it is recommended that amounts higher than 1 ml are used. If the urine proceeds directly to the uses and methods of the invention it is preferred that the urine is not stored longer than 24 h at room temperature. In case it should not be possible or desirable that the urine proceeds to the uses and methods of the invention within 24 h it is preferable to centrifuge the urine, discard the supernatant and store the frozen urine cell pellet until the (resuspended) cell pellet proceeds to the uses and methods of the invention (cf. the examples herein below for further details).

The term "diagnosing" as used herein is directed to the identification of a subject having a disease. In accordance with the invention the disease is transitional cell carcinoma.

The term "grading" as used herein is directed to the identification of the degree of cell anaplasia of a tumor cell in a subject which has been diagnosed as to have a tumor. The most commonly system used for grading tumors is the system according to the guidelines of the American Joint Commission on Cancer. As per these guidelines, the following grading categories are distinguished: GX (grade cannot be assessed), G1 (well-differentiated; low grade), G2 (moderately differentiated; intermediate grade), G3 (poorly differentiated, high grade); G4 (undifferentiated, high grade). In accordance with the invention the tumor is a transitional cell carcinoma.

The term "subject" in accordance with the invention refers to a mammal, preferably a domestic animal or a pet animal such as horse, cattle, pig, sheep, goat, dog or cat, and most preferably a human.

Generally LASP-1 levels of above 1 ng/500 μl of urine pellet allow the conclusion that a subject has a transitional cell carcinoma. In accordance with the first embodiment of the invention it is thus preferred that a LASP-1 level of above 1 ng/500 μl of urine pellet diagnoses a subject having a transitional cell carcinoma. It is also preferred with regard to the first embodiment of the invention that an increase of LASP-1 expression correlates with a higher grading of the transitional cell carcinoma.

The LASP-1 levels described herein may be determined, for example, by using a "molecule binding to LASP-1" and preferably a "molecule specifically binding to LASP-1". A molecule binding to LASP-1 designates a molecule which under known conditions occurs predominantly bound to LASP-1. Preferably, the dissociation constant $K_D$ of the complex formed by said molecule and the target molecule is less than $10^{-3}$ M. More preferred $K_D$ is less than $10^{-5}$ M, yet more preferred less than $10^{-7}$ M, and most preferred less than $10^{-9}$ M. Binding involves in general interaction(s) between one or more moieties or functional groups of the binding molecule and one or more moieties or functional groups of LASP-1, wherein said interaction may comprise one or more of charge-charge interactions; charge-dipole interactions; dipole-dipole interactions, wherein said dipoles may be permanent, induced or fluctuating; hydrogen bonds; and hydrophobic interactions. Hydrogen bonds and interactions involving a permanent dipole are of particular relevance in the sense that they confer specificity of binding by their directional character.

Binding may be unspecific, for example by interaction with a group such as a charge or a dipole, which may be present many times at the surface of the target molecule. Preferably, binding is specific, i.e., it occurs at a defined site of LASP-1 and goes along with the formation of a network of several distinct and specific interactions. Specific binding may occur with hardly any change of the conformation of the molecules involved ("key-in-lock"), or it may involve conformational changes of one or both of the binding partners ("hand-in-glove" paradigm). One or more binding molecules may bind to LASP-1. If more than one test molecule binds LASP-1, the binding molecules may either bind at the same site or at overlapping sites, giving rise to competitive binding, or bind to distinct sites such that no interference between the molecules binding to distinct sites of LASP-1 occurs. Accordingly, the term "complex" embraces binary complexes of the type (LASP-1):(binding molecule) and ternary complexes of the type (LASP-1):(first binding molecule):(second binding molecule) as well as complexes of a LASP-1 with more than two binding molecules. In cases, where more than one binding molecule is capable of binding to LASP-1, both binary and ternary (and higher order) complexes may be formed.

A "molecule binding to LASP-1" is preferably an antibody, aptamer, fragment or derivative thereof specifically recognizing LASP-1, or fragment or epitope thereof. Said antibody may be a monoclonal or a polyclonal antibody. The antibody is preferably a monoclonal antibody.

The term "antibody" as used herein includes monoclonal antibodies, polyclonal antibodies, single chain antibodies, or fragments thereof that specifically bind LASP-1, or fragment or epitope thereof, also including bispecific antibodies, synthetic antibodies, antibody fragments, such as Fab, Fd, F(ab)$_2$, Fv or scFv fragments etc., or a chemically modified derivative of any of these. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

Preferably, the antibody, aptamer, fragment or derivative thereof according to the invention specifically binds the LASP-1, or fragment or epitope thereof whose presence or absence is to be monitored.

The term "specifically binds" in connection with the antibody used in accordance with the present invention means that the antibody etc. does not or essentially does not cross-react with (poly) peptides or epitopes of similar structures. Cross-reactivity of a panel of antibodies etc. under investigation may be tested, for example, by assessing binding of said panel of antibodies etc. under conventional conditions (see, e.g., Harlow and Lane, (1988), loc. cit.) to the (poly) peptide of interest as well as to a number of more or less (structurally and/or functionally) closely related (poly) peptides. Only those antibodies that bind to the (poly) peptide/protein of interest (i.e. LASP-1, or fragment or epitope thereof) but do not or do not essentially bind to any of the other (poly)

peptides which are preferably expressed by the same cells as the (poly) peptide of interest, are considered specific for the (poly) peptide/protein of interest and selected for further studies in accordance with the use and method of the invention. It is particularly preferred that said antibody or antibody binding portion is or is derived from a human antibody or a humanized antibody.

The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

Aptamers are DNA or RNA molecules that have been selected from random pools based on their ability to bind other molecules. Aptamers have been selected which bind nucleic acid, proteins, small organic compounds, and even entire organisms. A database of aptamers is maintained at http://aptamer.icmb.utexas.edu/.

As is evident from examples below, the inventors have unexpectedly identified LASP-1 as a marker for transitional cell carcinoma in urine samples. To the best knowledge of the inventors, the use of LASP-1 as a marker for TCC overcomes several limitations of the diagnostic of TCC available from the prior art.

Cystoscopy and urinary cytology have an observer dependency and limitations. Furthermore, cystoscopy has a low patients acceptance. Current diagnostic markers cannot replace cystoscopy and/or urinary cytology, as they have a low specificity resulting in a high number of false positive results and unnecessary examinations, such as nmp22 or BTA stat [4].

LASP-1 expression is detected in fast proliferating cells, such as the mucosa of the stomach [11], in the tested cancer entities medulloblastoma, metastatic breast, ovarian and colon cancer [8-10, 14] and—as demonstrated now by the inventors herein by immunohistology—in urothelium of bladder and ureter. As it is evident from the examples below, in TCC an increased expression of LASP-1 is noted throughout the urothelium but this overexpression was only moderate when investigated by immunohistochemistry.

Measurement of LASP-1 content in urinary cell pellets is highly sensitive for TCC. A sensitivity of 83.1% and a specificity of 85.3% enable this protein to be a used for the detection and grading of TCC. According to the knowledge of the inventors such good performance was not found for any prior art marker for TCC. The high specificity advantageously reduces false positive results and, hence, unnecessary cystoscopies and biopsies and turns this marker into a striking new tool suitable to complement or supplement the current gold standard of cystoscopy and urine cytology.

Although the inventors do not wish to be bound by this hypothesis, it is believed that the reason for the increased LASP-1 content in the urine of patients with TCC is an increased shedding of tumor cells into the urine cells. An enhanced loss of e-cadherin and other adhesion molecules is well known in TCC [15] and in agreement with a lower detection rate for well differentiated tumors compared to more aggressive high grade tumors in urine cytology [1]. Therefore, it is tentative to speculate that LASP-1 further raises tumor cell shedding into the urine by a disassembly of focal adhesion contacts. Indeed, the examples herein show an impaired cell migration and increased adhesion after LASP-1 knockdown in bladder cancer cells. Therefore, increased LASP-1 content of urinary cell pellets in TCC may be explained by a higher content of tumor cells.

It should not go unnoted, that the total protein content of the cells in the urine sample (i.e. a urine cell pellet in accordance with the examples described herein) was not necessarily predictive for TCC. Despite low protein content in the urine sample few tumor patients showed high LASP-1 levels while some control volunteers with high overall protein content showed no LASP-1 staining in the Western Blots. Although, overall, tumor patients exhibited a higher number of cells in urine samples (evidenced by bigger urinary cell pellets) this difference was not precise enough for detection of TCC.

Initially, the finding of an abundant expression of LASP-1, both in healthy urothelium and TCC, was surprising. However, a strong and therefore easily visible overexpression of LASP-1 may not be necessary for its oncogenic function. For example, in breast cancer the pro-metastatic effect is not mediated by overexpression but by a nuclear localization of LASP-1 [8], and [6] reported a discrepancy between LASP mRNA expression and actual protein level. The authors of [6] hypothesize that LASP protein levels might be decreased by increased ubiquitination and proteolysis in some tumor cell lines. This finding might explain that in some murine bladder cancer cell lines LASP-1 expression was decreased while other studies report an increase of LASP-1 expression [16] [17]. The constitutively high expression of LASP-1 in highly proliferating cells may mask an increase or shift in localization pattern [11].

In summary, the inventors have unexpectedly found that measurement of urinary LASP-1 is an ideal marker for the detection and grading of TCC. The use of LASP-1 as marker for TCC can replace or augment the current gold standard for TCC-diagnosis, namely cystoscopy and urine cytology. The detection of LASP-1 in urine samples, may further help to reduce the numbers of cystoscopical evaluations in follow up examinations, e.g. for the grading of TCC.

The present invention furthermore relates to a method for diagnosing transitional cell carcinoma comprising detecting the presence or absence of LASP-1 in a urine sample obtained from a subject, wherein the presence of LASP-1 above 1 ng/500 µl urine pellet is indicative for transitional cell carcinoma.

Traces of LASP-1 may also be found in urine samples obtained from healthy subject (i.e. in particular a subject not having transitional cell carcinoma). Though, the presence of LASP-1 above 1 ng/500 µl of urine pellet is to the best knowledge of the inventors indicative for transitional cell carcinoma.

The present invention also relates to a method for grading transitional cell carcinoma comprising determining the level of LASP-1 in a urine sample obtained from a subject, wherein the level of LASP-1 correlates with the grade of the transitional cell carcinoma.

By correlation analysis of LASP-1 content with the grading of transitional cell carcinomas the inventors revealed a clear increase of LASP-1 expression with higher grading. Thus, the LASP-1 contents correlate with the grading of the transitional cell carcinoma. The high urinary LASP-1 levels in increased tumor grades indicate that aggressive tumors exhibit a stronger LASP-1 expression. Migration and adhesion experiments underline this fact.

In accordance with a preferred embodiment of the invention the urine sample is unprocessed or processed (e.g stabilized) urine, a urinary cell pellet or a resuspended urinary cell pellet. The urine sample may be stabilized, for example, by adding substances which prevent cellular and in particular protein degradation within the urine sample. Such substances are well-know in the filed of medical diagnostics.

As it is evident from the examples herein below, a urinary cell pellet may, for example, be obtained by transferring 10 mL urine to a 15 mL tube and centrifuging at 3.300 g for 10 minutes to pellet the cells. The supernatant is poured off carefully so as not to disturb or dislodge the cell pellet. A resuspended urinary cell pellet (independent of quantity of the pellet) may, for example, be obtained by resuspending each pellet in 200 µl Laemmli sample buffer, heating at 95° C. for 5 min. The suspension may be stored at −20° C. until further processing.

In accordance with a further preferred embodiment of the invention the urine sample has been obtained from a subject not having a urinary tract infection.

The use of urinary LASP-1 measurement for detection or grading of TCC may give a false positive result if the urine sample is contaminated with leukocytes (i.e. a specific cell-type defending the body against infectious disease and foreign material). Leukocytes have a high cellular LASP-1 content. Therefore urine samples obtained from subjects with urinary tract infections are preferably excluded. The subjects' urine may then preferably be obtained when the infection was successfully treated.

In accordance with another preferred embodiment of the invention the urine sample comprises less than 250 erythrocytes per µl unprocessed urine, preferably less than 200 erythrocytes per µl unprocessed urine and more preferably less than 150 erythrocytes per µl unprocessed urine.

Also contamination with erythrocytes (i.e. red blood cells) above 250 erythrocytes per µl of unprocessed urine may give false positive results, due to the high cellular LASP-1 content of erythrocytes. In the examples described herein it has been found that only 19% of patients with TCC exhibited a hematuria (i.e. is the presence of erythrocytes) of 100-200/µl of unprocessed urine The other patients with TCC exhibited no hematuria or a hematuria of below 100-200/µl of unprocessed urine. According to current guidelines a hematuria is preferably to be further investigated, by cystoscopy [1].

As described in the examples, urine samples may be controlled for erythrocytes with urine sticks (Combur 10 Test M, Roche, Mannheim, Germany). Urine samples comprising erythrocytes may subjected to a cell-lysis step specifically lysing erythrocytes. Alternatively erythrocytes may be removed from a urine sample by magnetic beads specifically binding to surface marker of erythrocytes. Surface markers for erythrocytes are well-known and include, for example, glycophorin A (CD235a).

According to a different preferred embodiment of the invention the transitional cell carcinoma is transitional cell carcinoma of the urine bladder, pelvis of the ureter, ureter, urethra, urachus, kidney or combination thereof.

As it is detailed herein above the transitional cell carcinoma may affect one or more of these organs and organ appendages.

Furthermore, in accordance with another preferred embodiment of the invention the detection of LASP-1 comprises Western Blot analysis, mass spectrometry analysis, FACS-analysis, and ELISA.

Western Blot analysis, mass spectrometry analysis, FACS-analysis, and ELISA are non-limiting examples of methods which may be used to qualitatively, semi-quantitatively and/or quantitatively detect LASP-1. In the examples herein below Western Blot analysis was used for the detection of LASP-1.

Western blot analysis is a widely used and well-know analytical technique used to detect specific proteins in a given sample, for example, a tissue homogenate or body extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Also mass spectrometry (MS) analysis is a widely used and well-know analytical technique, wherein the mass-to-charge ratio of charged particles is measured. Mass spectrometry is used for determining masses of particles, for determining the elemental composition of a sample or molecule, and for elucidating the chemical structures of molecules, such as proteins, peptides and other chemical compounds. The MS principle consists of ionizing chemical compounds to generate charged molecules or molecule fragments and measuring their mass-to-charge ratios.

Fluorescence activated cell sorting (FACS) analysis is a widely used and well-know analytical technique, wherein biological cells are sorted based upon the specific light scattering of the fluorescent characteristics of each cell. Therefore, cells were fixed in 4% formaldehyde, permeabilized with 0.2% Triton-X-100, and incubated with a fluorophore-labeled antibody (e.g. mono- or polyclonal LASP-1 antibody).

Enzyme-linked immunosorbent assay (ELISA) is a widely used and well-know sensitive analytical technique, wherein an enzyme is linked to an antibody or antigen as a marker for the detection of a specific protein.

In accordance with a further preferred embodiment of the invention the LASP-1 runs as a 38 kDa protein in Western Blots.

Human LASP-1 is preferably a protein having 261 amino acids (most preferably the 261 amino acids of NCBI protein accession number NP_006139.1 which is shown in SEQ ID NO: 1).

According to a preferred embodiment the method of the invention further comprises (i) an evaluation of an endoscopy of the urinary bladder via the urethra in the subject from which the urine sample has been obtained, and/or (ii) a cytology examination of the urine sample for abnormal cells.

At present cytoscopy (i.e. endoscopy of the urinary bladder via the urethra) and urinary cytology (i.e. cytology examination of the urine sample for abnormal cells) are mainly used in order to diagnose and grade transitional cell carcinoma. Although both diagnostic methods suffer from the limitations discussed herein, they may be useful to supplement the diagnosing and grading of transitional cell carcinoma by using LASP-1 as defined herein above.

In another embodiment the invention relates to a kit for diagnosing and/or grading transitional cell carcinoma comprising (a) means for the detection and/or quantification of LASP-1 in a urine sample obtained from a subject and (b) instructions for using the kit.

With regard to the instructions of the kit it is preferred that it is described therein that a LASP-1 level of above 1 ng/500 µl of (unprocessed or processed) urine diagnoses a subject having a transitional cell carcinoma. It is also preferred with regard to the instructions of the kit that it is described therein that an increase of LASP-1 expression correlates with higher grading of the transitional cell carcinoma.

The instructions may furthermore comprise information on the method of the detection of LASP-1. For example, information may be provided on assays based on protein detection. Such assays include without limitation enzyme-linked immunosorbent assay (ELISA), mass spectrometry, ion exchange chromatography, gel filtration chromatography, affinity chromatography, high pressure liquid chromatography (HPLC), reversed phase HPLC, disc gel electrophoresis, Western blot analysis, immunoprecipitation, see, for example, Soejima and Koda, Transfusion 45 (2005) 1934-1939; Yeh et al., Anesth. Analg. 101 (2005) 1401-1406; Chou et al., Am. J. Clin. Pathol. 124 (2005) 330-338. As it described herein above in greater detail, the detection of LASP-1 may, for example, comprise Western Blot analysis, mass spectrometry analysis and/or FACS-analysis.

In accordance with the kit, "means for the detection and/or quantification of LASP-1" preferably comprise a "molecule binding to LASP-1" and more preferably a "molecule specifically binding to LASP-1". Examples of molecules (specifically) binding to LASP-1 are described herein above in more detail.

In accordance with a preferred embodiment of the invention the means for the detection and/or quantification of LASP-1 is an antibody specifically binding to LASP-1

The Figures show:

FIG. 1 LASP-1 immunostaining in human bladder tissue. A and B: Normal bladder urothelium. C: Transitional cell carcinoma. Healthy tissue (thin arrows) and tumor (fat arrows). D: Transitional cell carcinoma. E and F: LASP-1 positive ureter sample. G: LASP-1 positive tumor cells (arrows) from a patient with bladder cancer and (H) from a healthy volunteer in cytospin specimen. All samples DAB, brown. Magnification 100× for A, C and E, all others 400×).

Figure 2:
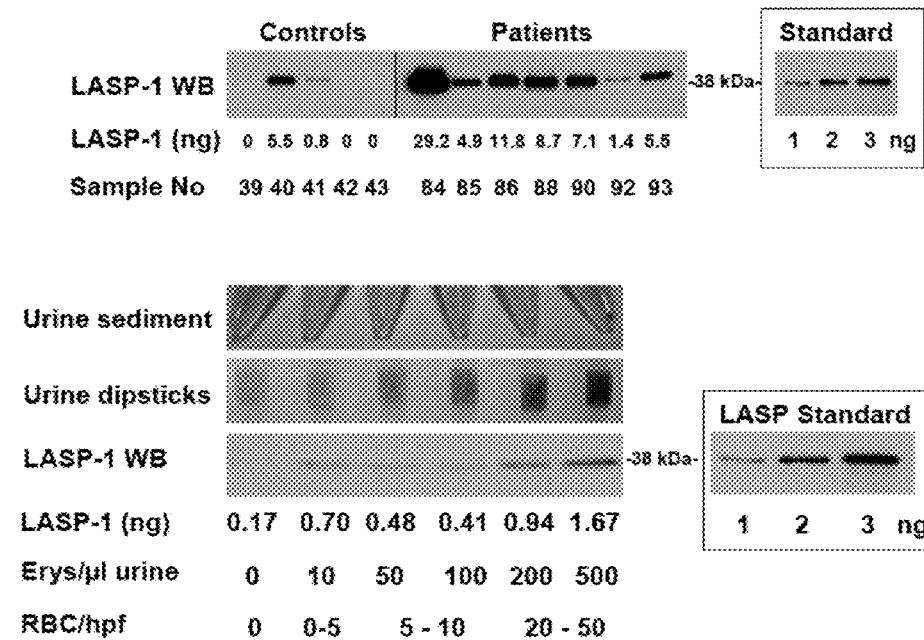

FIG. 2 A: Western Blot example of LASP-1 analysis and calculation in control and patient urine samples. B: Western Blot analysis and calculation of LASP-1 levels in urine samples contaminated with a fixed number of erythrocytes (Erys/μl urine), respectively, red blood cells per high-power field (RBC/hpf). Shown are also the corresponding urine dipsticks and the visible red blood cell pellets after sedimentation of the urine probes. Hematuria >200 Erys/μl urine are contraindicative.

Figure 3:
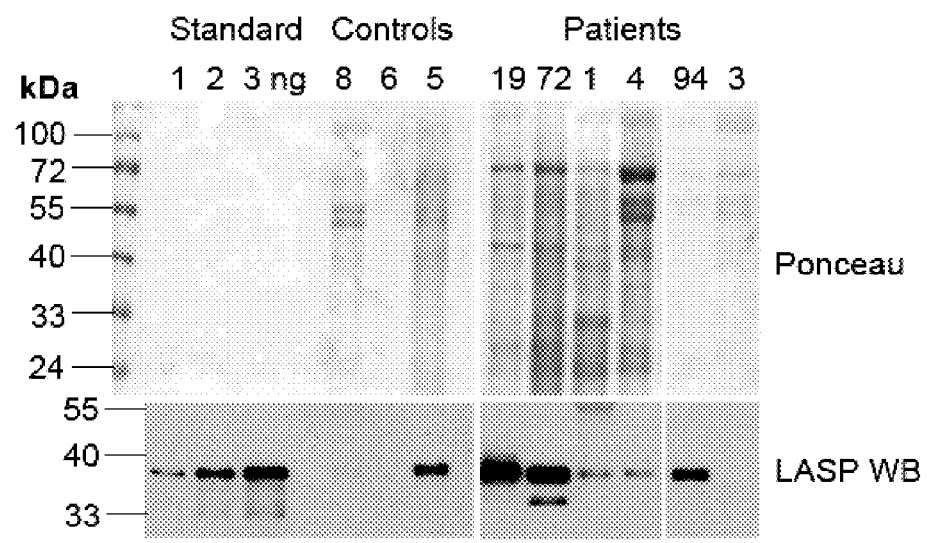

FIG. 3 Ponceau staining and LASP-1 Western Blot analysis of urinary pellets from control volunteers and TCC patients. LASP-1 protein concentrations are not necessarily related to overall protein amount of the probes.

Figure 4:
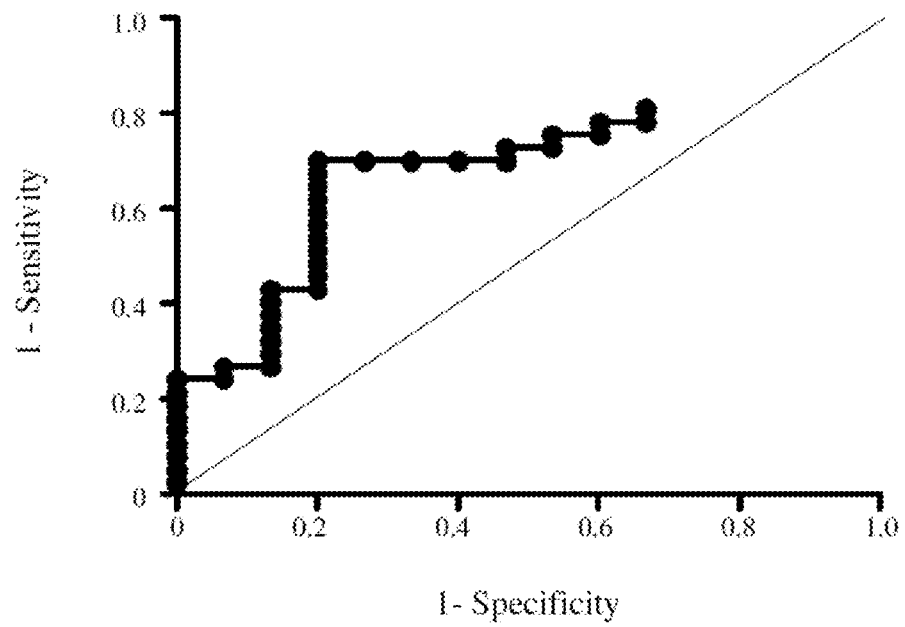

FIG. 4 Receiver operating characteristic (ROC)-analysis of urinary LASP-1 content in bladder cancer. Area under curve was 70.0% (95% confidence interval: 0.544 to 0.854).

Figure 5:
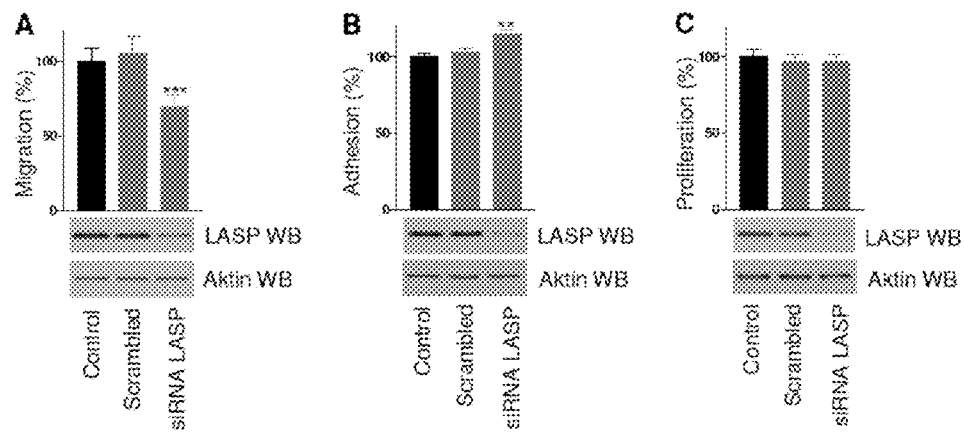

FIG. 5 A: LASP-1 knockdown inhibits cell migration. T24 bladder cancer cells transfected with LASP-1 siRNA and scrambled control siRNA were seeded in modified Boyden chambers and incubated for 4 h. Migrating cells were fixed with paraformaldehyde and stained with crystal violet. The absorbance was measured. Bars, SEM (n=6); * Students t test, p<0.0005; versus control. Experiments were performed three times with similar results. B: Increased adhesion in LASP-1-depleted cells. T24 bladder cancer cells were seeded in 48 well plates coated with fibronectin and incubated for 4 h. Cells were fixed with paraformaldehyde and stained with crystal violet. Absorbance was measured at 595 nm. Bars, SEM (n=8);  Students t test; p<0.001, versus control. C: LASP-1 knockdown does not influence cell proliferation. LASP-1 siRNA-transfected T24 cells were seeded in 48 wells, incubated with MTT/dye solution for 4 h and the absorbance was recorded. Bars, SEM. Experiments were performed three times with similar results.

The examples illustrate the invention. For all experiments, LASP-1 knockdown efficiency was controlled by Western blots.

EXAMPLE 1

Materials and Methods

Tissue collection and immunohistochemistry Patients background and clinicopathologic characteristics are summarized in Table 1.

TABLE 1

Patients characteristics

| Pathologic T stage | No of patients | Pathologic grading | No of patients |
|---|---|---|---|
| Ta | 35 | G1 | 7 |
| Tcis | 17 | G2 | 35 |
| T1 | 8 | G3 | 30 |
| T2 | 7 | Total | 72 |
| T3 | 3 | | |
| T4 | 2 | | |
| Total | 72 | | |

| Pathologic T stage | No of patients | Pathologic grading | No of patients |
|---|---|---|---|
| Healthy donors | 48 | Healthy donors and T0 | 69 |
| T0 | 21 | G1 | 23 |
| Ta | 33 | G2 | 15 |
| Tcis | 1 | G3 | 25 |
| T1 | 13 | Total | 132 |
| T2 | 14 | | |
| T3 | 0 | | |
| T4 | 2 | | |
| Total | 132 | | |

The samples were staged according to the Union Internationale Contre Ie Cancer (UICC). Paraffin-embedded tissue samples of 72 archived human urinary bladder with confirmed histological diagnoses and 17 incidental healthy ureter samples from patients undergoing nephrectomy for renal cell cancer were obtained from the Department of Pathology, University of Wuerzburg.

Immunohistochemistry

For immunohistochemical staining procedures two tissue sections were cut from each regular paraffin embedded tissue at 2-3 μm. For immunostaining, sections were placed onto APES (3-amino-propyltriethoxy-silane; Roth, Karlsruhe, Germany) coated slides, dewaxed in xylene, rehydrated in graded ethanol and in TRIS-buffered saline (TBS; 25 mM TRIS/HCl, pH 7.4, 137 mM NaCl, 2.7 mM KCl). For antigen retrieval, sections were subjected to heat pretreatment by boiling it in 0.01 M of sodium citrate buffer (pH 6.0) for 10 min in a microwave oven (600 Watt/sec.). Endogenous peroxidase was blocked by incubation in 0.1% hydrogen peroxide in PBS for 5 min. Slides were then incubated with the polyclonal anti-LASP-1 antibody [12] diluted 1:1000 in "antibody diluent" (DAKO, Hamburg, Germany) followed by EnVision/rabbit detection system (DAKO, Hamburg, Germany). For Hematoxylin (HE)-staining, 3,3'-Diaminobenzidine (DAB; DAKO, Hamburg, Germany) was used as chromogen and sections were counterstained in hematoxylin (Mayers, Sigma, Deisenhofen, Germany), dehydrated through graded ethanol and embedded in Entelan (Merck, Darmstadt, Germany). All HE samples were examined by an expert pathologist to confirm the previous diagnosis. All immunohistological samples were evaluated by the pathologist (A.S.) and an independent observer for defining of the percentage of LASP-1 positive cells and the staining intensity. Scoring of cytosolic LASP-1 expression was carried out in analogy to scoring of hormone receptor Immune Reactive Score (IRS), ranging from 0-12 according to Remmele et al. and is described in detail for LASP-1 in breast cancer cells [9, 13].

Patient Population for Urine Analysis

In total 48 healthy volunteers and 84 patients undergoing either cystectomy for verified muscle invasive TCC or transurethral resection for suspected bladder tumor in the two major urological departments in Wuerzburg and Freiburg were included. LASP-1 content of urinary cell pellet was measured in 132 cases and urine dipsticks analyses performed in parallel. Exclusion criteria were gross hematuria and urinary infection. Approvals of the local ethic committees in Freiburg and Wuerzburg were obtained. All participants gave written informed consent.

Western Blot Analysis for Urinary LASP-1

From all urine samples, 10 ml of urine was centrifuged immediately at 3.300 g for 10 min at RT in a 15 ml tube. Independent of quantity, each pellet was resuspended in 200 µl Laemmli sample buffer, heated at 95° C. for 5 min and stored at −20° C. for further processing. Of each sample, 10 µl (corresponding to 500 µl urine) were resolved by 10% SDS-PAGE. After blotting on nitrocellulose membrane and blocking with 3% nonfat dry milk in 10 mM Tris, pH 7.5, 100 mM NaCl, 0.1% (w/v) Tween 20, the membrane was first incubated with the antibody raised against LASP-1 (1:10000) [12] followed by incubation with horseradish peroxidase-coupled goat anti-rabbit IgG (Biorad, Munich, Germany), diluted 1:5000, and visualization was done using ECL (GE Healthcare, Freiburg, Germany). Protein bands were visualized by autoradiography. Quantification of autoradiography signals was carried out by densitometry using the ImageJ software (NIH, Bethesda, USA).

To determine release of LASP-1 from urothelial cells into the urine, 200 µl supernatant samples were processed in parallel for Western blot analysis.

To analyse the influence of hematuria two healthy donor urine samples were supplemented with increasing amounts of fresh blood imitating erythrocytes contamination in the range of 10-500 cells/µl urine. Samples were controlled with urine sticks (Combur 10 Test M, Roche, Mannheim, Germany) and then processed as described above. Recombinant human LASP-1 served as standard concentration marker [12].

Statistical Analysis

Sensitivity, specificity, as well as positive and negative predictive values of urinary LASP-1 levels were investigated after setting a cut off level by ROC-analysis. Confidence interval was 95%. All analysis were performed with GraphPad Prism 5.

Cell Line and Culture Conditions

The human bladder carcinoma cell line T24 (purchased from ATCC) was grown at 37° C. under 5% $CO_2$ atmosphere in McCoy medium (Invitrogen, Karlsruhe, Germany) containing 10% heat-inactivated fetal bovine serum (PAA, Linz, Austria) and 1% streptomycin/ampicillin (Invitrogen, Karlsruhe, Germany).

Suppression of LASP-1

LASP1 knock-down was performed using two siRNA constructs targeting the LASP1 sequences 5'-AAG GTG AAC TGT CTG GAT AAG-3' (bases 49-69) and 5'-AAG CAT GCT TCC ATT GCG AGA-3' (bases 80-100); (ordered from Dharmacon, Lafayette, Colo.). Both siRNA exhibited LASP-1 knockdown of 75-80%. Non-targeting siRNA #5 from Dharmacon was used as scrambled control. Cells were plated at a density of $2\times10^5$ cells/25 $cm^2$ flask, grown for 24 h at a confluence of 30-50% and transfected with 30 µl siRNA stock solution mixed with 30 µl HiPerfect (Qiagen, Hilden, Germany) in 100 µl reduced serum medium OPTI-MEM-I (Gibco, Paisley, UK) according to the manufacturers protocol. After 4 h incubation at 37° C., transfection medium was replaced by 5 ml routine cell culture medium and incubation was continued for 42 h. For scrambled control cells, 30 µl non-targeting siRNA (20 µM) was used. For adhesion and migration experiments, the cells were synchronized by starving overnight in basal medium with 0.5% FCS. At least three independent experiments were performed for each cell line, and representative results are shown. LASP1 knockdown was controlled by Western blots in all experiments.

Adhesion, Proliferation and Migration Experiments

To assess cell adhesion, 48-well plates were coated with 10 µg/ml fibrinogen (Sigma, Deisenhofen, Germany) diluted in PBS and 0.1% BSA overnight at 4° C. Cells were washed in serum-free medium, re-suspended at a concentration of $5\times10^5$ cells/ml and 200 µl were seeded. Cells were allowed to attach for 4 h at 37° C. Non-adherent cells were removed by gentle washing with PBS. Attached cells were fixed in 4% (w/v) paraformaldehyde for 10 min and then stained with 0.5% (w/v) crystal violet (in 2% ethanol, filtered with 0.45 µM pore size) for 20 min followed by 3 times washing with PBS. The blue dye was eluted in 10% acetic acid for 10 min, and the absorbance was measured at 595 nm on a plate reader. Adhesion assays were performed in 3 independent experiments with both LASP-1 siRNAs, each with 6 replicates Proliferation was determined by the MTT-based CellTiter96 AQ Non-Radioactive Cell Proliferation Assay (Promega, Mannheim, Germany). In brief, cells were seeded at $1\times10^4$ cells/48-well and cultured overnight at 37° C. After 24 h, cells were transfected with LASP1-specific siRNA and cultured for another 48 h. Transfection reagent and scrambled siRNA controls were included in all experiments. After the incubation period, 30 µl MTT dye solution was added. After an incubation of 4 h at 37° C., 200 µl STOP-solution (0.1 N HCl, 10% SDS) was added and the plates were incubated at RT for another hour. Cells were solubilized by pipetting, transferred to a 96-well plate and the absorbance was recorded using a plate reader. Cell proliferation was expressed as percentage of control cells. Experiments were done twice with both LASP-1 siRNAs in 8 replicates using separate cell cultures.

The migration assay was performed using a modified Boyden chamber assay (Transwell chambers, Corning Star, Cambridge, Mass.). In brief, cells were serum-starved overnight, trypsinized, adjusted for viability, counted and re-suspended in serum-free medium with 1 mM $MgCl_2$ to a concentration of $1\times10^6$ cells/ml. The lower surface of the filter membrane (8 µM pore size) was overlayed with 100 µl fibronectin solution (5 µg/ml; Sigma, Deisenhofen, Germany) as a chemoattractant for 30 min before adding 100 µl cell suspension into the BSA-coated filter chamber. The filter chambers were cultured in 500 µl routine medium with 10% FCS for 4 h at 37° C. to allow the cells to migrate through the porous membrane. Cells remaining at the upper surface were completely removed using a cotton swab. Cells at the lower surfaces of the membranes were stained in a solution of 1% (w/v) crystal violet in 2% ethanol for 30 s and rinsed afterwards in distilled water. Cell-associated crystal violet was extracted by incubating the membrane in 200 µl 10% acetic acid for 20 min and measured at 595 nm absorbance using a 96-well plate reader. Experiments were done twice in quadruplicate with both LASP-1 siRNAs.

EXAMPLE 2

LASP-1 Expression is Ubiquitous and Moderately Elevated in TCC in Immunohistochemistry The immunohistochemical distribution of LASP-1 in bladder cancer specimen of 72 patients undergoing either transurethral resection or cystectomy was investigated.

Only 6 samples out of these 72 TCC were attested to be LASP-1 negative determined by the intensity of the staining. All other tumors were stated LASP-1 positive. A consistant basal level of LASP-1 expression was noted in the surrounding healthy urothelium (FIGS. 1A-D). In order to analyse urothelium without a possible precancerous influence healthy urothelium from incidental ureter samples and observed a consistent LASP-1 expression throughout the urothelium was stained (FIGS. 1E and 1F). Analysis of the Immune Reactive Score showed that expression in TCC was higher than in the surrounding tissue or healthy tissue of the ureter but differences were only moderate, regardless of tumor cell grading.

EXAMPLE 3

Urinary LASP-1 is a Sensitive Marker for TCC

In order to investigate the presence of LASP-1 in voided urine of bladder cancer patients and to establish the diagnostic/prognostic possibilities of this marker protein, a total of 132 urinary sediments for the presence of LASP-1 by Western blot analysis was analysed. Pellets corresponding to 500 µl urine were separated by SDS-gel and LASP-1 concentration was determined according to the standard by densitometry. The cut-off point was set to 1 ng LASP-1/500 µl urine by ROC analysis, see below. In FIG. 2A a representative Western blot with LASP-1 standard, control samples and patient samples is shown. While only control sample No. 40 is false positive, all patients exhibit a detectable LASP-1 band >1 ng/500 µl urine at 38 kDa. LASP-1 protein levels are not necessarily related to overall protein amount of the probes (FIG. 3).

It should be noted that urine cytology (cytospin) as well as exfoliative bladder wash did not further enhance the diagnostic specificity of LASP-1 for TCC mostly due to insufficient cell counts but also because of only moderate differences in LASP-1 staining between healthy and tumor cells (FIGS. 1G and 1H).

To assess whether soluble LASP-1 is secreted into the urine of bladder cancer patients, additional Western blot analysis with the urine supernatant from 3 patients with low (0.18 ng/500 µl urine), medium (1.8 ng/500 µl urine) and high (7.8 ng/500 µl urine) LASP-1 levels in the urine sediment was performed. Soluble LASP-1 was not detected in any of the urinary supernatant probes (data not shown).

As microscopic hematuria is a common condition in bladder cancer it was sought to assess cross-reactivity of the LASP-1 antibody with contaminated protein from blood cells in the urinary sediment. Freshly-voided urine from two healthy volunteers without any medications and added blood to the urine to give known concentrations of hematuria was used. Urine was controlled by dipsticks and high-power field microscopy (hpf). As seen in FIG. 2B, blood up to 100 erythrocytes/µl urine (5-10 RBC/hpf) is by definition negative for LASP-1 (<1 ng) in the Western blot. Only after a red blood cell concentration beyond 200 erythrocytes/µl urine a weak LASP-1 band (>1 ng) was detected and a clearly visible red pellet could be observed in the urine sediment (FIG. 2B).

To determine the ideal cut off point for urine LASP-1 content a ROC analysis was performed on the results of the first 52 samples and determined an ideal cut off point of 1 ng LASP-1/500 µl (FIG. 4). Area under curve was 70.0% (95% confidence interval: 0.544 to 0.8537). Using this value, sensitivity and specificity for detection of TCC was 83.1% and 85.3%, respectively. Positive and negative predictive value was 83.1% and 80.6%, respectively (Table 2). Sensitivity for low vs high grade tumors was 65% and 87%. Sensitivity for non-muscle invasive tumors was 74% and for muscle invasive tumors 94.1%. A correlation analysis of LASP-1 content with grading revealed a clear increase of LASP-1 expression with higher grading (data not shown). In hematuria negative patients, sensitivity and specificity were 79.2 and 84.8%, respectively.

TABLE 2

Diagnostic value of LASP-1 measurement in urine sediment

| Number of patients | LASP-1 <1 ng 500 µl | LASP-1 >1 ng 500 µl | Total |
|---|---|---|---|
| TCC | 14 | 50 | 64 |
| No TCC | 57 | 11 | 68 |
| Total | 71 | 61 | 132 |

| | |
|---|---|
| Sensitivity | 83.1% |
| Specificity | 85.3% |
| Positive predictive value | 83.1% |
| Negative predictive value | 80.6% |

EXAMPLE 4

In Vitro Inhibition of LASP-1 Attenuates the Malignant Phenotype of Bladder Cancer Cells and Reduces Cell Detachment Cell migration, adhesion and proliferation was investigated in the human bladder cancer cell line T24 to investigate the reason for the increased LASP-1 content in urinary cell pellets. siRNA-mediated knockdown caused profound reduction of LASP-1 protein abundance in the cell line and was confirmed by Western Blot with maximum knock down≥80% detected after 48 hours (FIG. 5).

By using a modified Boyden-chamber and a fibronectin adhesion assay, a reduction in migratory potential (FIG. 5A) accompanied by an enhanced cell adhesion in T24 cells upon LASP-1 knockdown was observed (FIG. 5B), whereas no significant inhibition of proliferation was observed by the MTT assay in the cells upon LASP-1 knock down (FIG. 5C).

LITERATURE

1. Babjuk M, Oosterlinck W, Sylvester R, et al: EAU guidelines on non-muscle-invasive urothelial carcinoma of the bladder, the 2011 update. European urology 59:997-1008
2. Cooksley C D, Avritscher E B, Grossman H B, et al: Clinical model of cost of bladder cancer in the elderly. Urology 71:519-525, 2008
3. Pisipati S, Hu J, Pearce I: Patients' acceptance of repeated invasive urological investigations. BJU international 103: 1453-1454, 2009
4. Tilki D, Burger M, Dalbagni G, et al: Urine Markers for Detection and Surveillance of Non-Muscle-Invasive Bladder Cancer. European urology
5. Grunewald T G, Butt E: The LIM and SH3 domain protein family: structural proteins or signal transducers or both? Molecular cancer 7:31, 2008

6. Chiyomaru T, Enokida H, Kawakami K, et al: Functional role of LASP1 in cell viability and its regulation by microRNAs in bladder cancer. Urologic oncology
7. Pappas C T, Bliss K T, Zieseniss A, et al: The Nebulin family: an actin support group. Trends in cell biology 21:29-37
8. Frietsch J J, Grunewald T G, Jasper S, et al: Nuclear localisation of LASP-1 correlates with poor long-term survival in female breast cancer. British journal of cancer 102:1645-1653
9. Grunewald T G, Kammerer U, Kapp M, et al: Nuclear localization and cytosolic overexpression of LASP-1 correlates with tumor size and nodal-positivity of human breast carcinoma. BMC cancer 7:198, 2007
10. Zhao L, Wang H, Liu C, et al: Promotion of colorectal cancer growth and metastasis by the LIM and SH3 domain protein 1. Gut 59:1226-1235
11. Chew C S, Parente J A, Jr., Zhou C, et al: Lasp-1 is a regulated phosphoprotein within the cAMP signaling pathway in the gastric parietal cell. The American journal of physiology 275:C56-67, 1998
12. Butt E, Gambaryan S, Gottfert N, et al: Actin binding of human LIM and SH3 protein is regulated by cGMP- and cAMP-dependent protein kinase phosphorylation on serine 146. The Journal of biological chemistry 278: 15601-15607, 2003
13. Remmele W, Stegner H E: [Recommendation for uniform definition of an immunoreactive score (IRS) for immunohistochemical estrogen receptor detection (ER-ICA) in breast cancer tissue]. Der Pathologe 8:138-140, 1987
14. Traenka C, Remke M, Korshunov A, et al: Role of LIM and SH3 protein 1 (LASP1) in the metastatic dissemination of medulloblastoma. Cancer research 70:8003-8014
15. Patriarca C, Colombo P, Pio Taronna A, et al: Cell discohesion and multifocality of carcinoma in situ of the bladder: new insight from the adhesion molecule profile (e-cadherin, Ep-CAM, and MUC1). International journal of surgical pathology 17:99-106, 2009
16. Yao R, Lemon W J, Wang Y, et al: Altered gene expression profile in mouse bladder cancers induced by hydroxybutyl (butyl)nitrosamine. Neoplasia (New York, N.Y. 6:569-577, 2004
17. Grunewald T G, Kammerer U, Winkler C, et al: Overexpression of LASP-1 mediates migration and proliferation of human ovarian cancer cells and influences zyxin localisation. British journal of cancer 96:296-305, 2007
18. Mihlan S, Reiβ C, Thalheimer P, Herterich S, Gaetzner S, Kremerskothen J, Pavenstädt H J, Lewandrowski U, Sickmann A, Butt E. Nuclear import of LASP-1 is regulated by phosphorylation and dynamic protein-protein interactions. Oncogene. 2012 Jun. 4. doi: 10.1038/onc.2012.216. [Epub ahead of print] PubMed PMID: 22665060.

The invention claimed is:

1. A method for diagnosing urinary bladder transitional cell carcinoma in a human subject suspected of having urinary bladder cancer comprising:

(a) obtaining urine from the human subject wherein the human subject does not have urinary tract infection, (b) obtaining a pellet from the urine; and (c) detecting in the pellet the presence or absence of human LASP-1 (LIM and SH3 Domain Protein 1) consisting of the amino acid sequence of SEQ ID NO: 1 by Western Blot analysis, immunohistochemistry, mass spectrometry analysis, FACS analysis or ELISA, wherein the presence of LASP-1 above 1 ng/500 ul of the urine is indicative for urinary bladder transitional cell carcinoma and wherein the urine comprises less than 250 erythrocytes/ul.

2. The method of claim 1, further comprising:

(d) evaluating urinary bladder via the urethra using endoscopy in the subject from which the urine has been obtained, and/or (e) examining the urine for abnormal cells using cytology.

3. The method of claim 1, wherein LASP-1 is detected by Western Blot analysis, wherein LASP-1 is detected as a 261 amino acid protein that runs as a 38 kDa protein in Western blots.

* * * * *